(12) United States Patent
Hoelz et al.

(10) Patent No.: US 9,604,017 B2
(45) Date of Patent: Mar. 28, 2017

(54) NEEDLE FOR PIERCING A POWDER CAPSULE FOR INHALATION

(75) Inventors: Hubert Hoelz, Oberheimbach (DE); Stefan Lustenberger, Gensingen (DE); Torsten Kuehn, Appenheim (DE); Herbert Wachtel, Ingelheim am Rhein (DE); Rolf Kuhn, Ingelheim am Rhein (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 1942 days.

(21) Appl. No.: 11/560,267

(22) Filed: Nov. 15, 2006

(65) Prior Publication Data

US 2007/0107722 A1    May 17, 2007

(30) Foreign Application Priority Data

Nov. 15, 2005 (DE) .................. 10 2005 054 383

(51) Int. Cl.
*A61M 15/00* (2006.01)
(52) U.S. Cl.
CPC ...... *A61M 15/0035* (2014.02); *A61M 15/003* (2014.02); *A61M 15/0026* (2014.02); *A61M 15/0028* (2013.01); *A61M 15/0033* (2014.02)
(58) Field of Classification Search
CPC .......... A61M 15/0028; A61M 15/0033; A61M 15/003; A61M 15/0035
USPC ............ 128/200.24, 203.15, 203.12, 203.21, 128/203.19
See application file for complete search history.

(56) References Cited

U.S. PATENT DOCUMENTS

| 3,807,400 | A |   | 4/1974  | Cocozza |
|-----------|---|---|---------|---------|
| 3,955,558 | A | * | 5/1976  | Fuisz ............................ 600/573 |
| 3,991,761 | A |   | 11/1976 | Cocozza |
| 4,069,819 | A |   | 1/1978  | Valentini |
| 4,338,931 | A | * | 7/1982  | Cavazza .................. 128/203.15 |
| 4,541,427 | A | * | 9/1985  | Koss ........................ 128/207.29 |
| 4,889,114 | A |   | 12/1989 | Kladders |
| 5,207,658 | A | * | 5/1993  | Rosen et al. .................. 604/272 |
| 5,263,475 | A | * | 11/1993 | Altermatt et al. ....... 128/203.15 |
| 5,601,475 | A |   | 2/1997  | Stametz et al. |
| 5,607,401 | A | * | 3/1997  | Humphrey .................... 604/239 |
| 5,673,686 | A |   | 10/1997 | Villax |

(Continued)

FOREIGN PATENT DOCUMENTS

| CA | 2064860 A1 | 2/1991 |
| DE | 3345722 A1 | 6/1985 |

(Continued)

OTHER PUBLICATIONS

International Search report for PCT/EP2006/068356 mailed on Mar. 2, 2007.

(Continued)

*Primary Examiner* — Justine Yu
*Assistant Examiner* — Colin W Stuart
(74) *Attorney, Agent, or Firm* — Michael P. Morris; Philip I. Datlow (57) ABSTRACT

The invention relates to a powder inhaler with at least one specially sharpened needle, to ensure the precise piercing or cutting open of capsules and hence the optimum delivery of powdered medicament compositions, medicament formulations or medicament mixtures, as well as ensuring that little effort is needed to perforate or cut open the capsule.

15 Claims, 3 Drawing Sheets

(56) References Cited

U.S. PATENT DOCUMENTS

| | | | |
|---|---|---|---|
| 5,715,811 A * | 2/1998 | Ohki et al. | 128/203.21 |
| 5,881,721 A | 3/1999 | Bunce | |
| 5,947,118 A * | 9/1999 | Hochrainer et al. | 128/203.15 |
| 6,092,522 A * | 7/2000 | Calvert et al. | 128/203.21 |
| 6,095,141 A * | 8/2000 | Armer et al. | 128/204.26 |
| 6,488,027 B1 | 12/2002 | Moulin | |
| 7,017,573 B1 * | 3/2006 | Rasor et al. | 128/200.24 |
| 7,252,087 B2 | 8/2007 | Wachtel | |
| 2001/0008637 A1 * | 7/2001 | Hochrainer et al. | 424/451 |
| 2004/0182388 A1 | 9/2004 | Djupesland | |
| 2006/0254583 A1 | 11/2006 | Deboeck | |
| 2007/0107722 A1 | 5/2007 | Hoelz et al. | |
| 2010/0300440 A1 | 12/2010 | Deboeck | |

FOREIGN PATENT DOCUMENTS

| | | |
|---|---|---|
| DE | 202004005618 | 12/2004 |
| DE | 202004005618 U1 | 12/2004 |
| EP | 0147755 A2 | 7/1985 |
| EP | 0582276 A1 | 2/1994 |
| EP | 666085 A1 | 8/1995 |
| EP | 869079 A2 | 10/1998 |
| EP | 0911047 A1 | 4/1999 |
| EP | 1603615 A1 | 12/2005 |
| FR | 2146202 A1 | 3/1973 |
| JP | 8206210 A | 8/1996 |
| JP | 2001346879 A | 12/2001 |
| JP | 3308418 B2 | 7/2002 |
| JP | 2004526540 | 9/2004 |
| WO | 9102558 A1 | 3/1991 |
| WO | 9945987 A1 | 9/1999 |
| WO | 0051672 A1 | 9/2000 |
| WO | 02092154 A1 | 11/2002 |
| WO | 03080163 A1 | 10/2003 |
| WO | 2004082750 A1 | 9/2004 |
| WO | WO 2004/002750 A1 | 9/2004 |
| WO | 2005044353 A1 | 5/2005 |
| WO | 2007057362 A1 | 5/2007 |

OTHER PUBLICATIONS

Abstract in English for DE202004005618 publication date Dec. 9, 2004.

* cited by examiner

NEEDLE FOR PIERCING A POWDER CAPSULE FOR INHALATION

CROSS REFERENCE TO RELATED APPLICATIONS

This application claims priority to German application DE 10 2005 054 383, filed Nov. 15, 2005, which is incorporated herein in its entirety.

BACKGROUND OF THE INVENTION

1. Field of the Invention

The invention relates to a powder inhaler having at least one specially sharpened needle for the precise piercing or cutting open of capsules and hence for the optimum delivery of powdered medicament compositions, medicament formulations or medicament mixtures.

2. Description of the Prior Art

Powder inhalers are known from the prior art. For example, EP 0 703 800 B1 and EP 0 911 047 A1 disclose a powder inhaler consisting of a dish-shaped lower part and an equally dish-shaped cover. After placing the capsule in the capsule holder the patient can press an actuator which is movable from a resting position and thereby cooperates with at least one needle that can be pressed into the capsule holder. The capsule is pierced by the needle or needles and the drug is released.

Other inhalers are known by the brand names Spinhaler®, Rotahaler®, Aerolizer®, Flowcaps®, Turbospin®, AIR DPI®, Orbital®, Directhaler® and/or described in DE 33 45 722, EP 0 591 136, DE 43 18 455, WO 91/02558, FR-A-2 146 202, U.S. Pat. No. 4,069,819, EP 666085, EP 869079, U.S. Pat. No. 3,991,761, WO99/45987, WO 200051672, Bell, J. Pharm. Sci. 60, 1559 (1971); Cox, Brit. Med. J. 2, 634 (1969).

In medicine, needles are known for all kinds of applications, whether for diagnosis (biopsies), treatment (injection) or for perforating or cutting open capsules which are used in inhalers.

When perforating or cutting open a capsule, in contrast to perforating human or animal skin, it is always particularly important to produce a large, precise puncture hole for releasing the powder from the capsule as completely as possible.

A precise puncture hole or cut cannot be obtained using a blunt needle as experience has shown that this will only indent and damage the capsule. It would not then be possible to deliver the powder and hence the medicament, medicament formulation or medicament mixture.

The needle must also be specially sharpened for perforating or cutting open a capsule precisely, so as to ensure that the powder is subsequently expelled as completely as possible.

German Standard DIN 13097 contains ground rules for types of sharpening for medical cannulas for injection and transfusion from rigid and semi-rigid materials. These types of sharpening are simple, faceted and relief-ground sharpening. In addition there is the European standard EN ISO 7864 for sterile single-use injection cannulas.

Special needles for puncturing medicament capsules for use in powder inhalers are known for example from German Utility Model DE 20 2004 005 618. These are solid material needles with a bevelled basic point and two front faceted points with specially defined sharpening angles.

The task of the capsules is to protect the entire inhalable formulation that contains the active substance from chemical or physical changes before a patient inhales the formulation.

The capsule generally consists of two parts, a capsule body (body) and a capsule cap (cap), which are fitted together telescopically. However, multi-part capsules are also known.

The capsule material is a gelatin, particularly hard gelatin. For certain special applications, easily digested water-soluble plastics are used as the capsule material for use in humans, so as to release the active substance in certain parts of the gastro-intestinal tract when it is administered by oral route.

The following are examples of different capsule materials:

EP 0460921 describes capsules of chitosan and starch, cereal powder, oligosaccharides, methacrylic acid methyl acrylate, methacrylic acid ethyl acrylate, hydroxypropylmethylcellulose acetate, succinate or phthalate. The capsule material is characterised in that the contents are only released in the large intestine.

GB 938828 discloses capsules for radioactive substances used therapeutically or diagnostically. The capsules consist of water-soluble gelatine, methylcellulose, polyvinylalcohol or water-soluble non-toxic thermoplastics.

WO 00/07572 discloses capsules for inhalers, which consist of non-digestible plastics.

SUMMARY OF THE INVENTION

The aim of the invention is to provide a powder inhaler having at least one needle which has been specially sharpened for the accurate perforation or cutting open of a capsule so as to expel a defined amount of a medicament composition, a medicament formulation or mixture from the capsules used in powder inhalers.

This aim is achieved with a powder inhaler according to claim 1. Advantageous further features are the subject of the subsidiary claims.

The aim of the invention is also to provide a needle which by its specially sharpened shape ensures an improved expulsion of medicament compositions, medicament formulations or medicament mixtures, by precisely perforating or cutting open the capsule in the powder inhaler, with reduced effort required on the part of the patient.

The aim is achieved with a needle according to claim 14. Advantageous further features are the subject of the subsidiary claims.

DESCRIPTION OF THE INVENTION

As already mentioned above, numerous needles and types of sharpening are known from the prior art.

One basic condition which militates against applying the prior art to the present problem is the filling of the capsule with a pharmaceutical formulation.

Another basic condition is the dimensions and wall thickness of the capsules which are to be perforated or cut open and, in this case, in particular, the thin wall of such a capsule. This is necessary as the capsule must be suitable for use in a standard commercial inhaler. There, it must be capable of being pierced or cut open easily without any great effort on the part of the patient.

Figure 1:
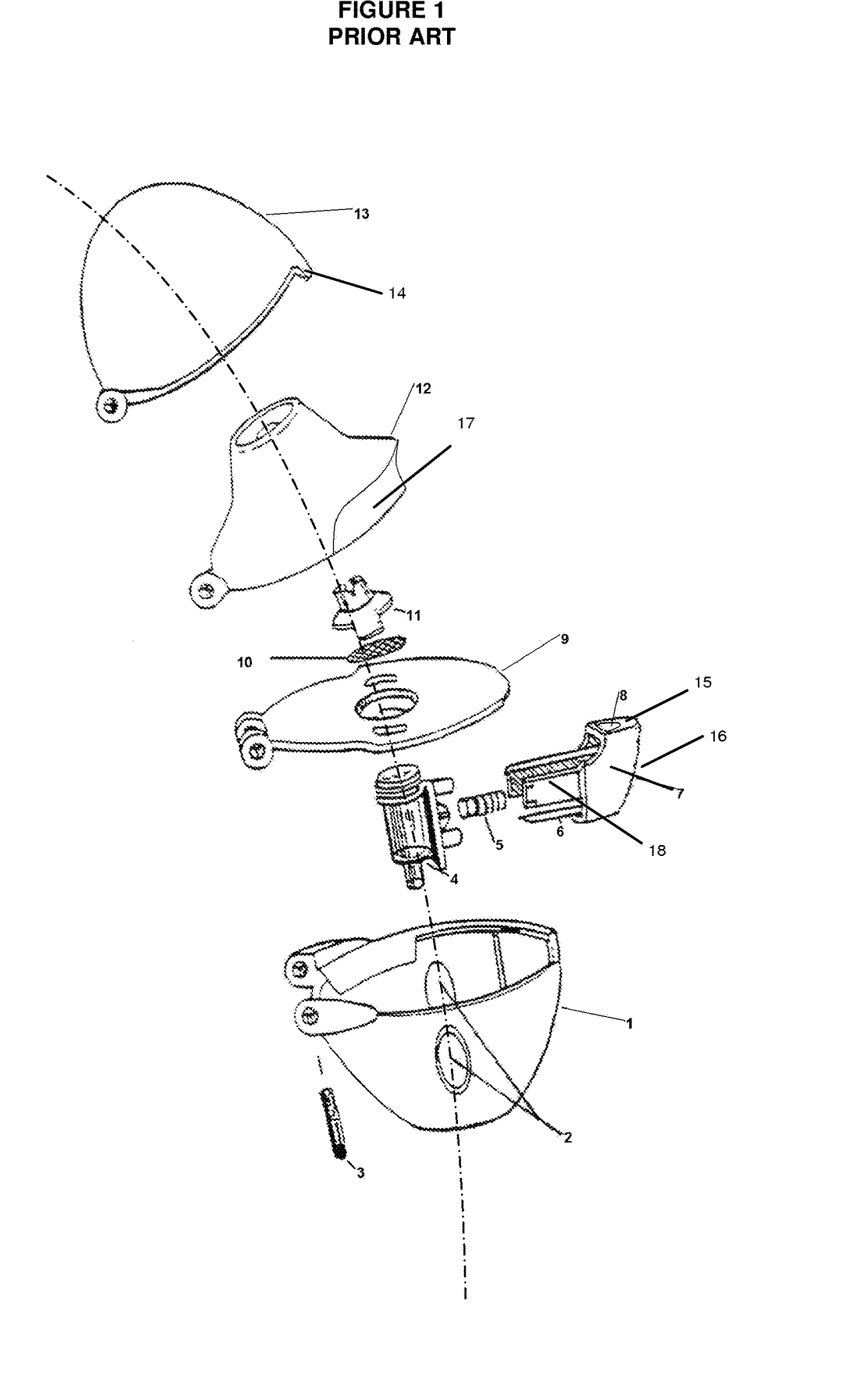
FIG. 1 is an inhaler for the inhalation of powdered medicament compositions and a two-part capsule.

The present invention preferably relates to a set comprising an inhaler for the inhalation of powdered medicament compositions and a two-part capsule, the inhaler being characterised by a) a cup-shaped lower part (1) open at the top, which comprises in its outer wall two opposing windows (2) and has a first hinge element with an articulation pin (3) at the edge of the opening, b) a plate (9) which covers the opening of the lower part (1) and comprises a second hinge element, and also carries a screen holder (11) with a screen (10), c) a capsule holder (4) which can be lowered for receiving the capsule, which is formed perpendicularly to the plane of the plate on the side of the plate (9) facing the lower part, and on which is provided a head which is movable counter to a spring, the head being provided with one or two sharpened pins (6), d) a mouthpiece (12) with a mouth tube and optionally a gripping aid (17) and a third hinge element, as well as e) a cover (13) which comprises a fourth hinge element, the hinge elements (one) of the lower part, (two) of the plate, (three) of the upper part and (four) of the cover being joined together. In addition the inhaler has an actuating member (7) which serves to open the cover (13), the closure element (14) on the cover (13) making contact with the inclined side wall (15) (optionally with a rifled surface (16)) of the recess (8), which acts as a sliding surface as the actuating member (7) is advanced further and releases the cover (13).

The guiding of the needle or needles is essentially effected by two laterally mounted guide arms (18). The guide arms also have the task of keeping the actuating member (7) under pre-tension. For this purpose the guide arms (18) are provided, at their end remote from the main body, with end stops which abut on the guide sleeves of the capsule holder (4) in the resting position of the actuating member (7). The guide sleeves are located on the outside of the capsule holder (4). Between the guide arms (18) is arranged a helical spring (5) which extends in its axial direction parallel to the needle or needles (6), while the helical spring (5) is matched to the length of the guide arms (18) such that the actuating member (7) is also pre-tensioned in the resting position. An inhaler of this kind is shown in FIG. 1.

The capsule is filled with a powdered inhalable medicament composition, medicament formulation or medicament mixture, optionally additionally containing a carrier material.

The compounds specified below be used on their own or in combination in the apparatus according to the invention. In the compounds listed below W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. In addition, double or triple combinations of W may be combined and used in the apparatus according to the invention. Combinations of W mentioned by way of example would include:

- W denotes a betamimetic, combined with [an] anticholinergics, corticosteroids, PDE4-inhibitors, EGFR-inhibitors or LTD4-antagonists,
- W denotes an anticholinergic, combined with [a] betamimetics, corticosteroids, PDE4-inhibitors, EGFR-inhibitors or LTD4-antagonists,
- W denotes a corticosteroid, combined with [a] PDE4-inhibitors, EGFR-inhibitors or LTD4-antagonists
- W denotes a PDE4-inhibitor, combined with [a] EGFR-inhibitors or LTD4-antagonists
- W denotes an EGFR-inhibitor, combined with [a] LTD4-antagonists.

Examples of betamimetics preferably include compounds which are selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2 H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1-dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert.-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide

4-(2-{6-[4-(3-cyclopentanesulphonyl-phenyl)-butoxy]-hexylamino}-1-hydroxy-ethyl)-2-hydroxymethyl-phenol N-adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Equally preferred anticholinergics are selected from among the salts of formula AC-1

AC-1 wherein X— denotes an anion with a single negative charge, preferably an anion selected from among fluoride, chloride, bromide, iodide, sulphate, phosphate, methanesulphonate, nitrate, maleate, acetate, citrate, fumarate, tartrate, oxalate, succinate, benzoate and p toluenesulphonate, preferably an anion with a single negative charge, particularly preferably an anion selected from among fluoride, chloride, bromide, methanesulphonate and p-toluenesulphonate, particularly preferably bromide, optionally in the form of the racemates, enantiomers or hydrates thereof. Of particular importance are those medicament combinations which contain the enantiomers of formula AC-1-ene

AC-1-ene wherein X— may have the meanings given above. Other preferred anticholinergics are selected from the salts of formula AC-2

AC-2 wherein R denotes either methyl or ethyl and wherein X— may have the meanings given above. In an alternative embodiment the compound of formula AC-2 may also be present in the form of the free base AC-2-base.

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, while instead of the methobromide, the metho-X salts may be used wherein X may have the meanings given hereinbefore for X—.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
cyanomethyl 6-alpha,9-alpha-difluoro-11-beta-hydroxy-16-alpha-methyl-3-oxo-17-alpha-(2.2.3.3-tetramethylcyclopropylcarbonyl)oxy-androsta-1,4-diene-17-beta-carboxylate,
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, di hydrogen phosphates, pal mitates, pivalates or furoates. PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxyphenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine
optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

The LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane-acetic acid

[2-[[2-(4-tert-butyl-2-thiazolyl )-5-benzofuranyl]oxymethyl]phenyl]acetic acid optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate. By salts or derivatives which the above-mentioned LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethyl-amino)-1 oxo-2-buten-1-yl]amino}-7-cyclopropylmethoxy-quinazoline 4-[(3-chloro-4-fluorophenyl)amino]-6-{[4-(N,N-dimethyl-amino)-1 oxo-2-buten-1-yl]amino}-7-cyclopropylmethoxy-quinazoline 4-[(R)-(1-phenyl-ethyl)amino]-6-{[4-(morpholin-4-yl)-1 oxo-2-buten-1-yl]amino}-7-cyclopentyloxy-quinazoline 4-[(3-chloro-4-fluoro-phenyl)amino]-6-{[4-((R)-6-methyl-2 oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2 oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethyl-amino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-( 1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethyl-amino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethyl-amino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethyl-amino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethyl-amino)-1-oxo-2-buten-1-yl]amino}-7-[(S)-(tetrahydrofuran-2-yl)methoxy]-quinazoline 4-[(3-ethynyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinylcarbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl) quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N, N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2.2-dimethy1-6-oxo-morpholin-4-yl)-ethoxy]-7-methoxy-quinazoline 4-[(3-chloro-4-fluoro-phenyl)amino]-6-[2-(2.2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2.2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(methoxymethyl)carbonyl]-piperidin-4-yloxy}-7-methoxy-quinazoline
4-[(3-chloro-4-fluoro-phenyl)amino]-6-(piperidin-3-yloxy)-7-methoxy-quinazoline
4-[(3-chloro-4-fluoro-phenyl)amino]-6-[1-(2-acetylamino-ethyl)-piperidin-4-yloxy]-7-methoxy-quinazoline
4-[(3-chloro-4-fluoro-phenyl)amino]-6-(tetrahydropyran-4-yloxy)-7-ethoxy-quinazoline
4-[(3-chloro-4-fluoro-phenyl)amino]-6-((S)-tetrahydrofuran-3-yloxy)-7-hydroxy-quinazoline
4-[(3-chloro-4-fluoro-phenyl)amino]-6-(tetrahydropyran-4-yloxy)-7-(2-methoxy-ethoxy)-quinazoline
4-[(3-chloro-4-fluoro-phenyl)amino]-6-{trans-4-[(dimethylamino)sulphonylamino]-cyclohexan-1-yloxy}-7-methoxy-quinazoline
4-[(3-chloro-4-fluoro-phenyl)amino]-6-{trans-4-[(morpholin-4-yl)carbonylamino]-cyclohexan-1-yloxy}-7-methoxy-quinazoline
4-[(3-chloro-4-fluoro-phenyl)amino]-6-{trans-4-[(morpholin-4-yl)sulphonylamino]-cyclohexan-1-yloxy}-7-methoxy-quinazoline
4-[(3-chloro-4-fluoro-phenyl)amino]-6-(tetrahydropyran-4-yloxy)-7-(2-acetylamino-ethoxy)-quinazoline
4-[(3-chloro-4-fluoro-phenyl)amino]-6-(tetrahydropyran-4-yloxy)-7-(2-methanesulphonylamino-ethoxy)-quinazoline
4-[(3-chloro-4-fluoro-phenyl)amino]-6-{1-[(piperidin-1-yl)carbonyl]-piperidin-4-yloxy}-7-methoxy-quinazoline
4-[(3-chloro-4-fluoro-phenyl)amino]-6-(1-aminocarbonylmethyl-piperidin-4-yloxy)-7-methoxy-quinazoline
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethansulphonylamino-cyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline
4-[(3-ethynyl-phenyl)amino]-6-(tetrahydropyran-4-yloxy)-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2.2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine desloratidine and meclozine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

Moreover inhalable macromolecules may be used as disclosed in EP 1 003 478.

In addition, the compound from the group of the derivatives of ergot alkaloids, triptanes, CGRP-inhibitors, phosphodiesterase-V inhibitors, optionally in the form of the racemates, enantiomers or diastereomers thereof, optionally in the form of the pharmacologically acceptable acid addition salts, solvates and/or hydrates thereof.

Examples of ergot alkaloid derivatives are: dihydroergotamine, ergotamine.

The needle may be made of any material known to the skilled man. In particular, it may be made of the following materials:

impact-resistant plastics, for example POM (polyoxymethylene or polyformaldehyde), ABS (acrylonitrile-butadiene-styrene copolymer), PEEK (polyetheretherketone), pharmaceutically acceptable stainless steel, e.g. with the composition X5CrNi18-10, material number 1.4301. Alternatives are other A2 Cr—Ni steels of the V2A series, e.g. material number 1.4567 or 1.4541, as well as A4 Cr—Ni—Mo steels of the V4A series, for example material number 1.4404, 1.4401 or 1.4435.

The needle may be a solid needle or a hollow needle (cannula).

The sharpened point of the needle or needles in the inhaler according to the invention, on a solid needle or hollow needle, may be a so-called triangular point, as shown in the attached drawing.

The sharpened point of the needle or needles in the inhaler according to the invention, on a solid needle or hollow needle, may be a so-called relief-ground point, as is known in principle from German standard DIN 13097 relating to medical cannulas, dating from September 2002.

The sharpened point of the needle or needles in the inhaler according to the invention, on a hollow needle, may be a so-called faceted point, as is known in principle from German standard DIN 13097 relating to medical cannulas, dating from September 2002.

The following applies to all needles:

The needle diameter is preferably 1.00-2.00 mm with an ultralong, long, medium or short point. The point lengths are for example: short point=0.5-3 mm; medium point=4-7 mm; long point=8-11 mm; ultralong point=12-15 mm.

The inhaler according to the invention contains at least one needle, preferably two needles, for perforating or cutting open, preferably for perforating a capsule contained in an inhaler, for the inhalation of a medicament composition, a medicament formulation or medicament mixture, while the two needles may each take the form of a solid or hollow needle with a triangular or relief-ground point or in the form of a hollow needle with a faceted point.

It is preferable to use two triangular needles which are in the form of solid needles and are most preferably used to perforate a non-digestible plastics capsule. It is most particularly preferred to use a combination of a triangular needle and a relief-ground needle.

The following Examples show a clear correlation between the hole size in the capsule, the precision of the puncture point and the dosage delivered. The term "dosage delivered" is also known in the art as the "delivered dose" and refers to the amount of active substance expelled which is measured in the dosage collecting tube according to the Pharmacopeia.

In detail the delivered dose was determined by measuring the mass of the filled capsule and expelling the contents into the dosage tube according to Pharm. Eur., 4th edition (2002) p. 554 ff. (or USP for USA). Then the difference is weighed to determine the capsule mass filling compared with the capsule mass expelled.

In contrast to the delivered dose, the term "delivered mass" denotes the total amount of powder, i.e. incl. formulating material, which is delivered. The delivered mass is determined by weighing the full capsule by comparison with the emptied capsule and calculating the difference in weight.

Figure 2:
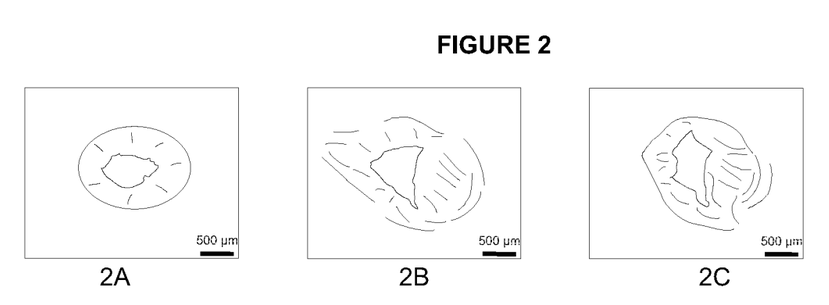
FIG. 2 shows the geometry of the perforations may be pencil-shaped needle (FIG. 2A), triangular needle (FIG. 2B), or square needle (FIG. 2C).

Referring to FIG. 2, the geometry of the perforations may be pencil-shaped needle (FIG. 2A), triangular needle (FIG. 2B), or square needle (FIG. 2C). The puncture location was examined under a Zeiss microscope, model Axioplan, and then photographed with an Olympus camera known by the trade mark DP10. The images and hence the holes were analysed using SIS Analysis Software, Version 3.0.

Figure 3:
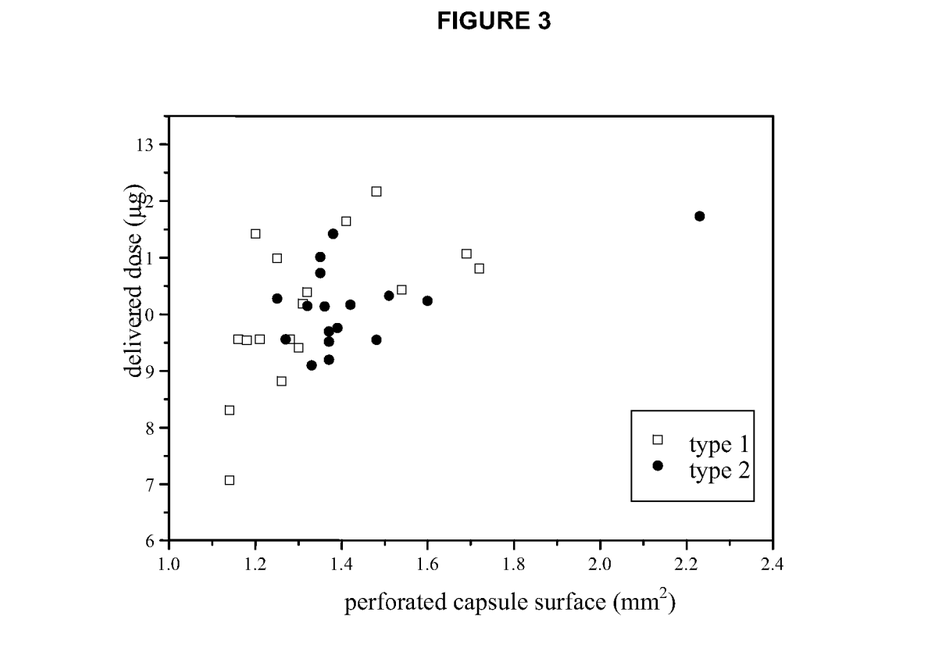
FIG. 3 shows the correlation between delivered dose and perforated capsule surface with relief-ground needles (solid needles). Two different types of needle were tested (type 1 and type 2).

Referring to FIG. 3, there is shown the correlation between delivered dose and perforated capsule surface with relief-ground needles (solid needles). Two different types of needle were tested (type 1 and type 2).

Figure 4:
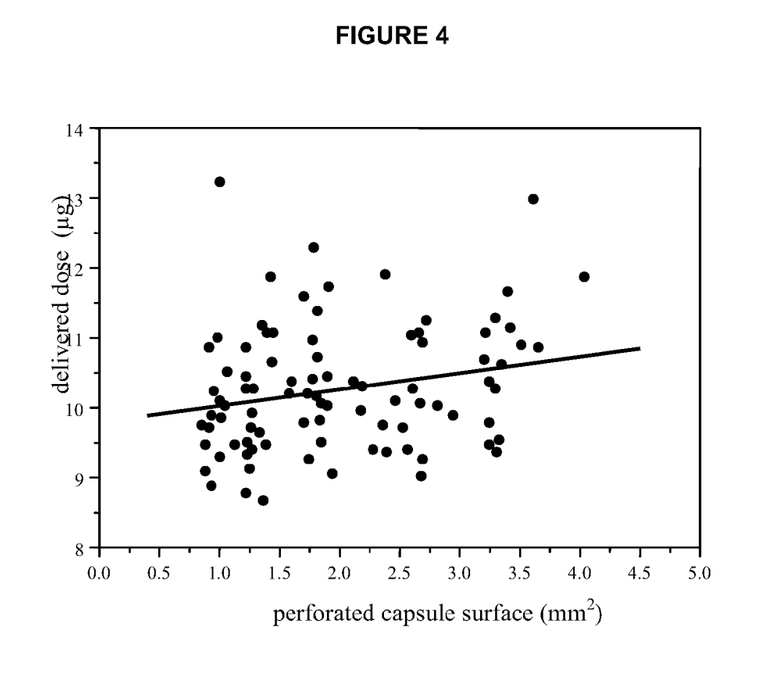
FIG. 4 shows the correlation between perforated capsule surface and delivered dose with faceted needles (solid needles). The line drawn through is a trend, determined by the least error squares method.

Referring to FIG. 4, there is shown the correlation between perforated capsule surface and delivered dose with faceted needles (solid needles). The line drawn through is a trend, determined by the least error squares method.

TABLE 1: Comparison of the different types of point:

The measurements were taken on 4 devices with 10 capsules each, after 10 capsules had been emptied in each device in a first practice run. The Delivered Mass (%) is the percentage ratio of the difference in mass (full capsule—emptied capsule)/fill mass.

Formula:

Delivered Mass (%)=100*(m(voll)−m(leer))/m(filling)

TABLE 1

| solid needle | number of measurements | mean of Delivered Mass (%) | variance (%$^2$) | standard deviation (%) |
|---|---|---|---|---|
| faceted | 40 | 83.1 | 96.0 | 9.8 |
| standard | 40 | 85.5 | 62.0 | 7.9 |
| triangular | 40 | 95.1 | 58.8 | 7.7 |

The advantage of the triangular needle is clearly a high delivered mass and a small standard deviation.

Figure 5:
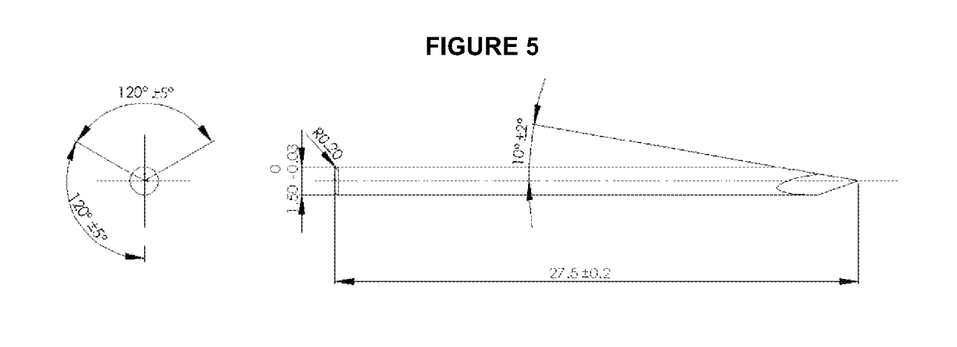
FIG. 5 shows a drawing of an embodiment of a needle by way of example.

Referring to FIG. 5, there is shown a drawing of an embodiment of a needle by way of example. As can be seen, the needle includes a solid substantially circular cross-section extending about a central longitudinal axis. The point of the needle is triangular, with very specific characteristics especially suited for puncturing, perforating and/or cutting into a capsule containing a powdered medicament. In particular, the point is defined by three substantially equally shaped bevels meeting at a tip. Notably, the tip is located on the central longitudinal axis.

We claim:

1. An inhaler for delivering a powdered medicament from a capsule, comprising: at least one needle having a diameter of 1.00-2.00 mm, a solid substantially circular cross-section about a central longitudinal axis, and a triangular point defined by three substantially equally shaped bevels meeting at a tip located on the central longitudinal axis, wherein the at least one needle operates to perforate or cut open the capsule by piercing the capsule and withdrawing therefrom to produce an aperture through which to release the powdered medicament.

2. The inhaler according to claim 1, wherein the point of the at least one solid needle is ultralong having a point length of 12-15 mm, long having a point length of 8-11 mm, medium having a point length of 4-7 mm or short having a point length of 0.5-3 mm.

3. The inhaler according to claim 1, wherein the at least one needle is formed from an impact-resistant plastics or a pharmaceutically acceptable stainless steel.

4. The inhaler according to claim 1, wherein the at least one needle of the inhaler comprises a combination of two such needles.

5. The inhaler according to claim 1, wherein the capsule is a plastic capsule.

6. The inhaler according to claim 1, wherein the at least one needle is used to perforate or cut open a capsule made of a non-digestible plastics.

7. An inhaler for delivering powdered medicament compositions from capsules, comprising:
a lower part,
a plate which can be latched to the lower part and with which the lower part can be closed off, and a capsule holder which can be lowered in the lower part in order to receive the capsules,
a mouthpiece latched to the plate,
a cover which covers the mouthpiece in a closed position and latches by means of a closure element, while the lower part, the plate, the mouthpiece and the cover are jointed to one another by a single joint, and
an actuating member which can be moved out of a resting position and thereby cooperates with at least one needle which can be pressed into the capsule holder, the needle having a diameter of 1.00-2.00 mm, a solid substantially circular cross-section about a central longitudinal axis, and a triangular point defined by three substantially equally shaped bevels meeting at a tip located on the central longitudinal axis,
wherein the at least one needle operates to perforate or cut open given ones of the capsules by piercing the capsules and withdrawing therefrom to produce an aperture through which to release the powdered medicament.

8. The inhaler according to claim 7, wherein the at least one needle point is ultralong having a point length of 12-15 mm, long having a point length of 8-11 mm, medium having a point length of 4-7 mm or short having a point length of 0.5-3 mm.

9. The inhaler according to claim 7, the at least one needle is formed from an impact-resistant plastic or a pharmaceutically acceptable stainless steel.

10. The inhaler according to claim 7, wherein the at least one needle of the inhaler comprises a combination of two needles, each needle having a diameter of 1.00-2.00 mm, a solid substantially circular cross-section about a central longitudinal axis, and a triangular point defined by three substantially equally shaped bevels meeting at a tip located on the central longitudinal axis.

11. The inhaler according to claim 7, wherein the at least one needle is used to perforate a capsule made of a non-digestible plastic.

12. A needle for perforating or cutting open capsules in powder inhalers in order to expel a medicament composition by piercing the capsules and withdrawing therefrom to produce apertures through which the medicament composition is released, the needle comprising a diameter of 1.00-2.00 mm, a solid substantially circular cross-section about a central longitudinal axis, and a triangular point defined by three substantially equally shaped bevels meeting at a tip located on the central longitudinal axis.

13. The needle according to claim 12, wherein the point of the needle is ultralong having a point length of 12-15 mm, long having a point length of 8-11 mm, medium having a point length of 4-7 mm or short having a point length of 0.5-3 mm.

14. The needle according to claim 12, wherein the needle is made of an impact-resistant plastic or a pharmaceutically acceptable stainless steel.

15. The needle according to claim 12, wherein the needle is used to perforate a non-digestible plastic capsule in the powder inhaler.

* * * * *